United States Patent [19]

Veale et al.

[11] Patent Number: 5,405,852

[45] Date of Patent: Apr. 11, 1995

[54] AMIDE DERIVATIVES

[75] Inventors: Chris A. Veale, Newark, Del.; Peter Warner, Macclesfield, England; Donald J. Wolanin, Orange, Conn.

[73] Assignee: Zeneca Limited, London, England

[21] Appl. No.: 71,624

[22] Filed: Jun. 3, 1993

[30] Foreign Application Priority Data

Jun. 4, 1992 [GB] United Kingdom ............... 9211783

[51] Int. Cl.6 ..................... A61K 31/44; C07D 471/06
[52] U.S. Cl. .................................... 514/292; 514/256; 544/333; 546/86
[58] Field of Search ................... 514/256, 292; 546/86; 544/333

[56] References Cited

U.S. PATENT DOCUMENTS

| | | | |
|---|---|---|---|
| 4,847,202 | 6/1989 | Powers | 435/184 |
| 4,910,190 | 3/1990 | Bergeson et al. | 514/19 |
| 4,929,736 | 5/1990 | Groutas | 548/341 |
| 5,232,928 | 8/1993 | Skiles | 514/291 |
| 5,270,301 | 12/1993 | Wolanin | 514/19 |

FOREIGN PATENT DOCUMENTS

0509769A2 10/1992 European Pat. Off. .
0528633A1 2/1993 European Pat. Off. .

OTHER PUBLICATIONS

Skiles, F. W. "Inhibition of Human Leukocyte Elastase (HLE) by N–Substituted Peptidyl Trifluoromethyl Ketones" *J. Med. Chem.* (1992), 35, 641–662.

*Primary Examiner*—Celia Chang
*Attorney, Agent, or Firm*—Robert J. Harris; Monte R. Browder

[57] ABSTRACT

The present invention relates to certain novel amide

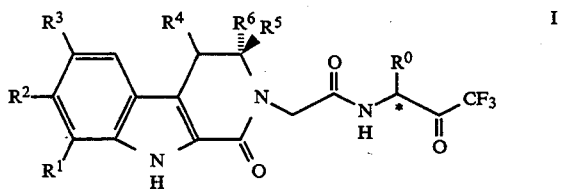

derivatives which are pyrido[3,4-b]indol-2-ylacetamides which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these amide derivatives, processes for preparing the amide derivatives, pharmaceutical compositions containing such amide derivatives and methods for their use.

12 Claims, No Drawings

AMIDE DERIVATIVES

The present invention relates to certain amide derivatives, in particular, certain pyrido[3,4-b]indol-2-ylacetamides, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these amide derivatives, processes for preparing the amide derivatives, pharmaceutical compositions containing such amide derivatives and methods for their use.

In U.S. Pat. No. 4,910,190, of 20 Mar. 1990, assigned to ICI Americas Inc. (now Zeneca Inc.), there is disclosed a series of peptidoyl trifluoromethane derivatives which are HLE inhibitors. Disclosed herein is a series of substituted 2-(1,2-dihydro-1-oxopyrido[3,4-b]indol-2-yl)-N-[3,3,3-trifluoro-1-(lower alkyl)-2-oxopropyl]acetamide derivatives, which unexpectedly possess inhibitory properties against HLE, which provides the basis for the present invention.

According to the invention there is provided a Compound of the invention which is a compound of formula I

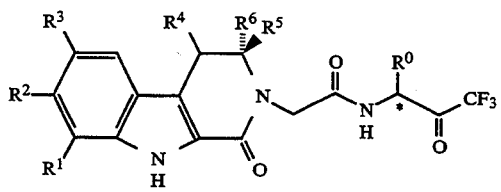

wherein:
$R^0$ is (1–5C)alkyl;
$R^1$ is selected from a group consisting of cyano, carbamoyl, formyl, hydroxy, (1–4C)alkoxy, methanesulfonyloxy, methanesulfonyl, (ReO)$_2$P(O), COORf, RgO-COO; and $R^2$ and $R^3$ are hydrogen; or
$R^1$ is hydrogen; $R^2$ is selected from a group consisting of hydrogen, XCOORh and XCONRiRj; and $R^3$ is selected from a group consisting of hydrogen, halogeno, hydroxy, (1–4C)alkoxy, (RkO)$_2$P(O), COORm and CONRnRp;
$R^4$ is hydrogen; and $R^5$ and $R^6$ are independently selected from a group consisting of hydrogen, (1–6C)alkyl, (3–6C)cycloalkyl or a radical of formula B.Y— in which B is aryl or heteroaryl and may bear an aryl or heteroaryl substituent and further in which B or an aryl or heteroaryl substituent on B may independently bear one or more substituents selected from the group consisting of amino, halogeno, nitro, (1–6C)alkyl, (3–6C)cycloalkyl, trifluoromethyl, cyano, hydroxy, (1–4C)alkoxy, lower acyloxy, SO$_2$Ra, COORb, CONRcRd; or
$R^4$ and $R^5$ together form a double bond, and $R^6$ is defined as above; and wherein
Rb-Rd, Rf, Rh-Rj and Rm-Rp are independently hydrogen or (1–4C)alkyl;
Re and Rk are independently selected from hydrogen, methyl or ethyl;
Ra and Rg are independently (1–4C)alkyl;
X is either a direct bond or is methylene; and
Y is a direct bond, methylene, ethylene, or trans-vinylene; or
for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such "propyl" embraces only the straight chain ("normal") radical, a branched chain isomer such as "isopropyl" being specifically referred to. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^0$ is isopropyl, a compound of formula I may be viewed as an valyl trifluoromethane derivative. In general, a compound of formula I having the (S)-configuration at the chiral center indicated by "*", which corresponds to the L-valyl configuration, is preferred as more potent than the corresponding (R)-isomer. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the facile epimerization of the chiral center indicated by "*" in formula I, it may be preferred to utilize a compound of formula I as a mixture of the (S)- and (R)-isomers at the center indicated by "*" in formula I.

It is preferred that the radicals $R^0$, $R^1$, $R^2$, $R^3$, $R^4$, $R^5$ and $R^6$ not contain nor introduce an additional element of chirality into the molecule beyond the chiral center indicated by "*" in formula I. It may also be preferred when $R^4$ and $R^5$ taken together do not form a double bond, for $R^5$ and $R^6$ to have the same value, since this avoids introducing additional chirality.

It is preferred when $R^4$ and $R^5$ are each hydrogen and $R^6$ has a value other than hydrogen, that the carbon bearing $R^6$ possess the absolute configuration depicted in formula I.

As will be appreciated by those skilled in the art, a trifluoromethyl ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

Particular values are listed below for radicals, substituents and ranges are for illustration only and they do not exclude other defined values or other values within defined ranges for the radicals and substituents.

One group of compounds of formula I is one in which $R^1$ is selected from a group consisting of cyano, carbamoyl, formyl, methanesulfonyloxy, methanesulfonyl, $(ReO)_2P(O)$, COORf and RgOCOO; and $R^2$ and $R^3$ are hydrogen; or $R^1$ is hydrogen; $R^2$ is selected from a group consisting of hydrogen, XCOORh and XCONRiRj; and $R^3$ is selected from a group consisting of hydrogen, halogeno, hydroxy, (1-4C)alkoxy, $(RkO)_2P(O)$, COORm and CONRnRp; and the values of the other radicals are as defined above.

A particular value for $R^0$ is ethyl or isopropyl.

A particular value for (1-4C)alkyl is methyl, ethyl, propyl, isopropyl, butyl, isobutyl, or tert-butyl. A particular value of (1-6C)alkyl is methyl, ethyl, propyl, isopropyl, butyl, isobutyl, tert-butyl, pentyl, 3-methylbutyl, 1-ethylpropyl, hexyl or 4-methylpentyl. A particular value of (3-6C)cycloalkyl is cyclopropyl, cyclopentyl or cyclohexyl. A particular value for aryl is phenyl, indenyl or naphthyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower acyloxy is acetoxy. A particular value for (1-4C)alkoxy is methoxy, ethoxy, propoxy, isproxy or t-butoxy. A particular value for halogeno is bromo, chloro or fluoro.

A particular value for $R^1$ is hydrogen, carboxy, formyl or methylsulfonyl. A particular value for $R^2$ is hydrogen, carboxymethyl or methoxy. A particular value for $R^3$ is hydrogen, dimethoxyphosphoryl or chloro. A particular value for $R^6$ is hydrogen, phenyl or isopropyl.

A more particular value for $R^0$ is isopropyl. A more particular value for $R^1$ is hydrogen or carboxy. A more particular value for $R^3$ is hydrogen or dimethoxyphosphoryl. A more particular value for $R^6$ is hydrogen or phenyl.

A particular group of compounds of formula I is one in which $R^0$ is isopropyl, $R^1$ is carboxy, $R^4$ and $R^5$ are hydrogen or taken together form a double bond, and $R^6$ is hydrogen or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl.

Another particular group of compounds of formula I is one in which $R^0$ is isopropyl, $R^1$ is hydrogen, $R^2$–$R^5$ have any of the values defined above and $R^6$ is phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl.

Specific compounds of formula I are described in the accompanying Examples.

Pharmaceutically acceptable salts of an acidic compound of formula I include alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. Pharmaceutically acceptable salts of a basic compound of formula I include acid-addition salts such as those made with a strong acid, for example hydrochloric, sulfuric or phosphoric acid, which acid provides a pharmaceutically acceptable anion.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II.

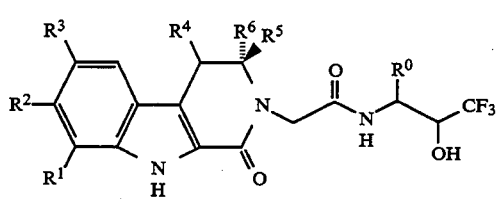

A convenient method is the use of excess dimethyl sulfoxide and a water soluble carbodimide, with dichloroacetic acid as a catalyst, in a inert-solvent such as toluene at about room temperature, for example as described in Example 1. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)-one with trifluoroacetic acid in dichloromethane.

(B) For a compound of formula I which bears a hydroxy substituent on an aryl or heteroaryl group, cleaving the alkyl ether or acyloxy ester of a corresponding compound of formula I which bears a (1–4C)alkoxy or lower acyloxy substituent on an aryl or heteroaryl group. Convenient methods include, for example, the cleavage of a methoxy group using boron tribromide, the cleavage of a tert-butoxy group using trifluoroacetic acid, and the acidic or alkaline hydrolysis of an acyloxy group.

(C) For a compound of formula I which bears a group of formula COORb, COORf, COORh or COORm in which Rb, Rf, Rh or Rm is hydrogen (a carboxy group), decomposing the ester group of a corresponding ester made with a conveniently removed acid protecting group. The decomposition may be carried out using any one of the variety of procedures well known in organic chemistry, for example basic hydrolysis using lithium or sodium hydroxide (as in Example 3), or by hydrogenolysis of a benzyl ester.

(D) For a compound of formula I in which $R^4$ and $R^5$ taken together form a double bond, dehydrogenation of a corresponding compound of formula I in which $R^4$ and $R^5$ are both hydrogen, using a conventional reagent such as for example 2,3-dichloro-5,6-dicyano-1,4-benzoquinone (as in Example 6).

(E) For a compound of formula I which contains an amino N—H residue, removal of the nitrogen protecting group of a corresponding compound bearing a conventional nitrogen protecting group by using a conventional method, for example, removal of a benzyloxycarbonyl group by hydrogenolysis, removal of a benzyloxycarbonyl or tert-butoxycarbonyl group by treatment with a strong acid, for example with trifluoromethanesulfonic acid in an inert solvent such as dichloromethane, or basic hydrolysis of a trifluoroacetyl group.

(F) For a compound of formula I which bears a heteroaryl N-oxide group, oxidation of a corresponding compound of formula I which bears a heteroaryl group using a conventional oxidant, such as for example dioxirane in acetone.

(G) For a compound of formula I which bears a primary amino group, reduction of a corresponding compound bearing a nitro group using a conventional reducing method, such as for example, hydrogenation over a palladium catalyst, or reduction with tin(II) chloride.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the 1-oxo tautomers, rather than the 1-hydroxy tautomers.

As will be clear to one skilled in the art, a variety of sequences are available for preparation of the starting materials including those shown in Scheme I and Scheme II (set out following the Examples).

In general, an indole ester of formula III can be protected and subsequently hydroyzed to give an acid of formula IV, in which Pg is an indole nitrogen protecting group such as, for example, benzyl, using conditions similar to those described in Example 1.b. Coupling of the acid with an appropriate amine of formula V, for example, using conditions similar to those described in Example 1.c., gives an amide of formula VI. Cyclization of a compound of formula VI, for example, using conditions similar to those described in Example 1.d., gives a lactam of formula VII. A compound of formula VII can be oxidized, to give an acid of formula VIII, coupled to give an amide of formula IX and deprotected to give an alcohol of formula II, for example, using steps similar to those described in Example 1.e.–1.g respectively.

Transformation of an anthranilic acid ester of formula X into a protected amine of formula XIII, in which Pz is an indole nitrogen protecting group such as for example benzyl, can be carried out using conditions similar to those described in Example 4.a.–4.b, as outlined in Scheme II. Coupling of a compound of formula XIII with an iodide as shown, gives a compound of formula XIV, in which Pa is an alcohol protecting group such as for example tert-butyldimethylsilyl. Introduction of a double bond, using for example conditions similar to those described in Example 4.d., gives a compound of formula XV. Deprotection of the alcohol functionality using, for example, conditions similar to those described in Example 4.e. gives a compound of formula II.

Alternatively, an alcohol of formula II wherein $R^4$ and $R^5$ are each hydrogen can be obtained directly from a compound of formula XIV by removal of the protecting groups Pz and Pa.

The trifluoromethyl amino alcohols required for the synthesis routes described above may be prepared by known procedures. For example, 3-amino-1,1,1-trifluoro-4-methyl-2-pentanol (as its hydrochloride salt) conveniently may be obtained as described in U.S. Pat. No. 4,910,190 in Example 4 (as a single diastereomer) or Example 6 (as a single enantiomer of a single diastereomer). If it is desired to carry out a chiral synthesis of a compound of formula I, using the single enantiomer in a substantially enantiomerically pure form and using methods and conditions which avoid epimerization at the center indicated by "*" in formula I provide such a synthesis.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

Inhibition Measurements

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. 4,910,190. Although some of the Compounds of the invention wherein $R^1$ and $R^6$ are hydrogen-exhibited $K_i$ values in the micromolar range, in general, the $K_i$ values for Compounds of the invention which were tested are generally on the order of $10^{-7}$M or much less. For example a $K_i$ of 27 nM was measured for the Compound of the invention described in Example 2.

Acute Lung Injury Model

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 μg), or by dosing them intravenously or orally as solutions at various times prior to the HLE challenge (100 μg) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid)-may be added as indicated to achieve solution. Compounds of this invention produced statistically significant reductions in wet lung weight and total lavagable cells relative to HLE alone.

Acute Hemorrhagic Assay

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141, 672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 μg/animal of HNE in 300 μL phosphate buffered saline (PBS) pH 7.4. Four hours after enzyme administration, the animals are killed with an overdose of . pentobarbital sodium, the thorax opened and the lungs and trachea removed. The excised lungs are lavaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (μL blood equivalents)/(mL lavage) are determined by comparing the OD of the test samples with the OD of the standard curve prepared from whole hamster blood. The total μL equivalents of blood recovered is determined by multiplying recovered lavage volume by the (μL blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which-HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In a liquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, an 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound-administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of the HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C;

(iii) chromatography means 'flash chromatography' (method of Still) carried out on Merck Kieselgel (Art 9385 from E. Merck, Darmstadt, Germany), elution using both step and ramp gradients is denoted by the parenthetical term "gradient" followed by the initial and final solvent ratios; thin layer chomatography (TLC) was carried out on 0.25 mm silica gel GHLF plates (Art 21521 from Analtech, Newark, Del., U.S.A.);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra; and, where examined, were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-$d_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

(xii) mass spectra (MS) were run with an electron energy of 70 electron volts in the chemical ionization mode using a direct exposure probe; where indicated ionization was effected by electron impact (EI) or fast atom bombardment (FAB); generally, only peaks which indicate the parent mass are reported.

EXAMPLE 1.
2-(8-Cyano-1-oxo-3-phenyl-1,2-dihydropyrido[3,4-b]indol2-yl)-N-(3,3,3-trifluoro-1-isopropyl-2-oxopropyl)acetamide To a solution of 2-(8-cyano-1-oxo-3-phenyl-1,2-dihydropyrido[3,4-b]indol-2-yl)-N-(3,3,3-trifluoro-2-hydroxy-1-isopropylpropyl)acetamide (0.3 g) in dimethyl sulfoxide (2 mL) and toluene (2 mL) was added 1-(3-dimethylaminopropyl)-3-ethylcarbodiimide hydrochloride (1.4 g) and dichloroacetic acid (0.23 mL), and the resulting solution was allowed to stir for 2 hours. The mixture was poured into ethyl acetate and was washed (1N hydrochloric acid, $H_2O$), dried, and evaporated. The resulting material was chromatographed, with methanol:dichloromethane (3:97) as the eluent, to give the title compound (0.23 g) as a yellow solid; TLC: $R_f$=0.5, methanol:dichloromethane (5:95);

NMR (DMSO/$H_2O$): 8.40 (d,1), 7.91 (d,1), 7.42 (s,5), 7.33 (t,1), 7.02 (s,1), 4.59 (m,2), 4.01 (d,1), 2.18 (m,1), 0.80 (d,3), 0.74 (d,3); MS: m/z=495(M+1).

Analysis for $C_{26}H_{21}F_3N_4O_3$: Calculated: C, 63.16; H, 4.28; N, 11.33; Found: C, 61.89; H, 4.53; N, 10.62.

The intermediate alcohol was prepared as follows:

a. Ethyl 7-cyanoindole-2-carboxylate. To a solution of ethyl 7-oxo-3a,8a,4,5,6,7-hexahydroindole-2-carboxylate (18.3 g) in benzene (50 mL) at 25° C. was added trimethylsilyl cyanide (13 mL) and zinc iodide (0.7 g). The resulting solution was allowed to stir for 4 hours, and was diluted with pyridine (125 mL). Phosphorus oxychloride (25 mL) was added and the mixture was heated for 3 hours at 80° C., cooled to room temperature, poured carefully into a solution of ice and 1N hydrochloric acid, and extracted into ether. The ether solution was dried and the solvent was evaporated. The crude material was dissolved in dioxane (200 mL) and to this was added 2,3-dichloro-5,6-dicyano-1,4-benzoquinone (22 g). After 3 hours the mixture was poured into ether, washed (saturated aqueous sodium bicarbonate, brine), dried, and evaporated. The resulting material was purified by chromatography, with ether:hexane as the eluent, to give the indole (15 g) as an off-white solid; TLC: $R_f$=0.4, ether:hexane (50:50); MS: m/z=215(M+1).

b. 1-Benzyl-7-cyanoindole-2-carboxylic acid. To a solution of ethyl 7-cyanoindole-2-carboxylate (0.54 g) in N,N-dimethylformamide (10 mL) was added sodium hydride (0,155 g, 60% dispersion in oil) and the solution was stirred for 0.5 hour. Benzyl bromide (0.33 mL) was added to the solution and the mixture was allowed to stir overnight. The solution was poured into saturated aqueous ammonium chloride and extracted into ether. The ether layers were washed (1N hydrochloric acid, $H_2O$, brine), dried, and evaporated to give an oil, which was dissolved in tetrahydrofuran (4 mL), methanol (2 mL), and $H_2O$ (2 mL). Lithium hydroxide (0.18 g) was added. After 1 hour the solvent was evaporated and the residue was diluted with $H_2O$ and made acidic to pH 2 by addition of 1N hydrochloric acid. This solution was extracted with ethyl acetate, and the organic layers were dried and evaporated to give the 1-benzyl compound (0.38 g) as a white solid; TLC: $R_f$=0.15, methanol:dichloromethane (10:90).

c. N-Allyl-1-benzyl-7-cyano-N-(2,2-diethoxy-1-phenylethyl)-2-indolecarboxamide. To a solution of 1-benzyl-7-cyanoindole-2-carboxylic acid (0.38 g) in dichloromethane (5 mL) was added oxalyl chloride (0.24 mL) and N,N-dimethylformamide (1 drop). The resulting solution was allowed to stir for 0.5 hour and the solvent was evaporated. The residue was dissolved in dichloromethane (5 mL) and to this was added N-allyl-2,2-diethoxy-1-phenylethylamine (366 mg), and triethylamine (0.4 mL). The resulting solution was allowed to stir overnight. The mixture was diluted with ethyl acetate, washed (1N hydrochloric acid, $H_2O$, brine), dried and evaporated. The crude material was purified by chromatography, with ether:hexane (30:70) as the eluent, to give the amide (0.44 g) as an oil; TLC: $R_f$=0.3, ether:hexane (30:70); MS: m/z=508(M+1).

The intermediate N-allyl-2,2-diethoxy-1-phenylethylamine was prepared as follows:

To a solution of 2,2-diethoxyacetophenone (42.38 g), allylamine (42.38 g), and activated 3A molecular sieves in ethanol (500 mL) was added ethereal hydrochloric acid until the pH was 6.5. The resulting suspension was allowed to stir for 3 hours. To this solution was added sodium cyanoborohydride (11.69 g) and the resulting solution was allowed to stir overnight. The reaction was made basic to pH 8 with 1N NaOH and filtered. The solvent was evaporated and the resulting material was diluted with ether, washed (1N aqueous NaOH), and dried. The solvent was evaporated and the resulting material was chromatographed, with ether:hexane (gradient, 10:90, 80:10) as the eluent, to provide the amine (36.5 g) as a yellow oil; TLC: $R_f$=0.3, ether:hexane (20:80); MS: m/z=250(M+1).

d. 2-Allyl-9-benzyl-8-cyano-3-phenylpyrido[3,4-b]indol-l(2H)-one. To a solution of N-allyl-1-benzyl-7-cyano-N-(2,2-diethoxy-1-phenylethyl)-2-indolecarboxamide (10.4 g) in ether (200 mL) at 25° C. was added concentrated sulfuric acid (3 mL) and the resulting solution was stirred for 3 hours. The reaction was quenched by addition of saturated aqueous sodium bicarbonate, diluted with ethyl acetate and washed with $H_2O$. The solution was dried and the solvent was evaporated to give a yellow solid. This solid was collected and washed with hexane to give the pyridoindole (7.5 g) as a yellow solid; TLC: $R_f$=0.4, ether:hexane (40:60);

NMR: 8.56 (d,1), 7.96 (d,1), 7.52 (s,1), 7.37 (t,1), 7.28 (m,9), 6.97 (d,1), 5.75 (m,3), 5.0 (d,1), 4.70 (d,1), 4.57 (d,1); MS: m/z=416(M+1).

e. 9-Benzyl-8-cyano-1-oxo-3-phenyl-1,2-dihydropyrido[3,4-b]indole-2-ylacetic acid. To a solution of 2-allyl-9-benzyl-8-cyano-3-phenylpyrido[3,4-b]indol-1(2H)-one (1.09 g) in tetrahydrofuran (26 mL) and $H_2O$ (3 mL) was added 4-methylmorpholine-N-oxide (0.34 g) and a catalytic amount of osmium tetroxide (4% solution in $H_2O$). The resulting solution was allowed to stir overnight. The reaction was quenched by addition of saturated aqueous sodium thiosulfate and filtered through diatomaceous earth. The solvent was evaporated. The residue was diluted with ethyl acetate and washed (1N hydrochloric acid, $H_2O$). The solution was evaporated and the resulting material was dissolved in ethanol (30 mL), and sodium periodate (0.73 g) in $H_2O$ (10 mL) was added. The solvent was evaporated and the residue was diluted with ethyl acetate, washed ($H_2O$), dried, and evaporated. The crude material was dissolved in tetrahydrofuran (10 mL), and tert-butyl alcohol (25 mL) and 2-methyl-2-butene (5.8 mL), along with a solution of sodium chlorite (3.15 g) and sodium dihydrogen phosphate in H$_2$O (10 mL), were added at 0° C. The solution was stirred for 0.5 hour, was quenched by addition of saturated aqueous sodium thiosulfate and evaporated. The residue was dissolved in H$_2$O and the pH adjusted to pH 3 with 1N hydrochloric acid. The solution was extracted with dichloromethane. The dichloromethane extracts were dried and evaporated to give an oil, which crystallized upon addition of ether to give the acid (0.88 g) as a yellow solid; TLC: R$_f$=0.4, methanol:-dichloromethane (15:85).

f. 2-(9-Benzyl-8-cyano-1-oxo-3-phenyl-1,2-dihydropryrido[3,4-b]indol-2-yl)-N-(3,3,3-trifluoro-2-hydroxy-1-isopropylpropyl)acetamide. To a solution of 9-benzyl-8-cyano-1-oxo-3-phenyl-1,2-dihydropyrido[3,4-b]indol-2-ylacetic acid (0.9 g), 3-amino-1,1,1-trifluoro-4-methyl-2-pentanol hydrochloride (0.65 g), 1-hydroxy-benzotriazole (0.57 g) and triethylamine (0.6 mL) in N,N-dimethyl-formamide (10 mL) was added 1-(3-dimethylaminopropyl)-3-ethylcarbodi-imide hydrochloride (0.5 g), and the resulting solution was allowed to stir overnight. The reaction mixture was poured into ether, washed (1N hydrochloric acid, 1N NaOH, H$_2$O), dried, and evaporated to give a yellow oil, which crystallized to give the alcohol (0.9 g) as a yellow solid; TLC: R$_f$=0.5, ether:hexane (80:20); MS: m/z=587(M+1).

g. 2-(8-Cyano-1-oxo-3-phenyl-1,2-dihydropyrido[3,4-b]indol-2-yl)-N-(3,3,3-trifluoro-2-hydroxy-1-isopropylpropyl)acetamide. To a solution of 2-(9-benzyl-8-cyano-1-oxo-3-phenyl-1,2-dihydropryrido[3,4-b]indol-2-yl)-N-(3,3,3-trifluoro-2-hydroxy-1-isopropylpropyl)- acetamide (2.0 g) in benzene (15 mL) at room temperature was added aluminum chloride (1.81 g) and the resulting mixture was allowed to stir for 1 hour. Additional aluminum chloride (1 g) was added and the mixture was allowed to stir until no starting material remained. The solution was poured into H$_2$O, and extracted into dichloromethane. The organic extracts were dried and evaporated. The resulting material was purified by chromatography, with dichloromethane:methanol (gradient, 100:0, 0:100) as the eluent, to give the deprotected amine (1.4 g) as a white solid; TLC: R$_f$=0.4, methanol:-dichloromethane (5:95); MS: m/z=497(M+1).

EXAMPLE 2.

2-(8-Formyl-1-oxo-3-phenyl-1,2-dihydropyrido[3,4-b]indol2-yl)-N-(3,3,3-trifluoro-1-isopropyl-2-oxopropyl)acetamide To a solution of 2-(8-formyl-1-oxo-3-phenyl-1,2-dihydropyrido[3,4-b]indol-2-yl)-N-(3,3,3-trifluoro-2-hydroxy-1-isopropylpropyl)acetamide (0.1 g) in dimethylsulfoxide (1 mL) and toluene (1 mL) was added 1-(3-dimethylaminopropyl)-3-ethylcarbodiimide hydrochloride (0.46 g) and dichloroacetic acid (0.1 mL). The resulting solution was allowed to stir for 2 hours. The mixture was poured into ethyl acetate, washed (1N hydrochloric acid, H$_2$O), dried, and evaporated. The resulting material was chromatographed, with ether-:ethyl acetate (gradient, 1:1, 0:1) as the eluent, to give the title compound (0.1 g) as a white solid; TLC: R$_f$=0.5, methanol:dichloromethane (5:95); 300 MHz.

NMR (DMSO/H$_2$O): 10.39 (s,1), 8.48 (d,1), 8.10 (d,1), 7.45 (m,6), 4.57 (m,2), 4.03 (d,1), 2.20 (m,1), 0.82 (d,3), 0.76 (d,3); MS: m/z=498(M+1).

Analysis for C$_{26}$H$_{22}$F$_3$N$_3$O$_4$: Calculated: C, 62.70; H, 4.45; N, 8.44; Found: C, 60.03; H, 4.37; N, 8.22.

The intermediate alcohol was prepared as follows.

To a solution of 2-(8-cyano-1-oxo-3-phenyl-1,2-dihydropyrido[3,4-b]indol-2-yl)-N-(3,3,3-trifluoro-2-hydroxy-1-isopropylpropyl)acetamide (0.5 g) and sodium hypophosphite hydrate (0.35 g) in pyridine (3 mL), acetic acid (1.5 mL), and H$_2$O (1.5 mL) was added a small amount of Raney nickel (50% slurry in water, pH greater than 9) and the resulting mixture was heated at 60° C. for 1 hour. Additional sodium hypophosphite hydrate (0.1 g) was added and the mixture was heated at 60° C. for 1 hour. The reaction mixture was diluted with methanol, filtered through diatomaceous earth, evaporated, and diluted with ethyl acetate. The resulting solution was washed with 1N hydrochloric acid, dried, and evaporated to give the aldehyde (0.4 g) as a yellow solid; TLC: R$_f$=0.45, methanol:dichloromethane (5:95);

NMR: 11.99 (s,1, indole NH), 10.53 (s,1, CHO).

EXAMPLE 3.

2-(8-Carboxy-1-oxo-3-phenyl-1,2-dihydropyrido[3,4-b]indol-2-yl)-N-(3,3,3-trifluoro-1-isopropyl-2-oxopropyl)acetamide To a solution of the product from Example 3.b. (0.17 g) in tetrahydrofuran (7 mL) and H$_2$O (1.5 mL) was added LiOH hydrate (0.04 g), and the resulting solution was allowed to stir for 3 hours. The solution was made acidic to pH 3 by addition of 1N hydrochloric acid and was extracted with dichloromethane. The organic layers were dried and the solvent was evaporated to give an off-white solid. This material was chromatographed with methanol:dichloromethane (gradient, 5:95, 10:90) as the eluent, to yield the title compound (0.1 g) as a tan solid; TLC: R$_f$=0.3, methanol:dichloromethane (10:90);

NMR (DMSO/D$_2$O): 8.12 (d,1), 7.94 (d,1), 7.41 (s,5), 7.24 (dd,1), 7.02 (s,1), 4.6 (broad s,2), 3.98 (broad s,1), 2.15 (m,1), 0.76 (m,6); MS: m/z=514(M+1).

The intermediate ester used in Example 3 was prepared as follows.

a. 2-(8-Methoxycarbonyl-1-oxo-3-phenyl-1,2-dihydropyrido[3,4-b]-indol-2-yl)-N-(3,3,3-trifluoro-2-hydroxy-1-isopropylpropyl)acetamide. To a solution of 2-(8-formyl-1-oxo-3-phenyl-1,2-dihydropyrido[3,4-b]indol-2-yl)-N-(3,3,3-trifluoro-2-hydroxy-1-isopropylpropyl)acetamide (0.26 g) in tert-butyl alcohol (7 mL), tetrahydrofuran (3 mL), and 2-methyl-2-butene (1.3 mL) was added a solution of sodium chlorite (0.5 g) and sodium dihydrogen phosphate (0.61 g) in H$_2$O (2 mL). The resulting solution was allowed to stir for 0.5 hour and the tetrahydrofuran was removed by evaporation. The solution was diluted with H$_2$O and made acidic to pH 3 by addition of 1N hydrochloric acid. The solution was extracted with dichloromethane and the organic layers were dried and evaporated. The residue was dissolved in ether (10 mL) and methanol (3 mL) and the solution was treated with ethereal diazomethane until a yellow color persisted. The excess diazomethane was quenched by addition of acetic acid and the solvent was evaporated. The resulting material was chromatographed, with methanol:dichloromethane (1:99) as the eluent, to give the ester (0.185 g); TLC: R$_f$=0.3, methanol:dichloromethane (1:99);

NMR: 10.91 (s,1, indole NH), 4.00 (s,3, CO$_2$CH$_3$).

b. 2-(8-Methoxycarbonyl-1-oxo-3-phenyl-1,2-dihydropyrido[3,4-b]-indol-2-yl)-N-(3,3,3-trifluoro-1-isopropyl-2-oxopropyl)acetamide. To a solution of the product from Example 3.a. (0.1 g) in dimethyl sulfoxide (1 mL) and toluene (1 mL) was added 1-(3-dimethylaminopropyl)-3-ethylcarbodiimide hydrochloride (0.34 g) and dichloroacetic acid (0.06 mL), and the resulting solution was allowed to stir for 2 hours. The mixture was poured into ethyl acetate, washed (1N hydrochloric acid, $H_2O$), dried and evaporated. The resulting material was chromatographed, with ether as the eluent, give the ketone (0.90 g) as a white solid; TLC: $R_f$=0.65, methanol:dichloromethane (2:98); MS: m/z=528(M+1).

It is noted that the product of Example 3.b. is also a compound of the invention.

EXAMPLE 4.

2-(8-Ethoxycarbonyl-1,2-dihydropyrido[3,4-b]indol-2-yl)-N-(3,3,3-trifluoro-1-isopropyl-2-oxopropyl)acetamide To a solution of 2-(8-ethoxycarbonyl-1,2-dihydropyrido[3,4-b]indol-2-yl)-N-(3,3,3-trifluoro-2-hydroxy-1-isopropylpropyl)acetamide (0.57 g) in dimethyl sulfoxide (6 mL) and toluene (6 mL) was added 1-(3-dimethylaminopropyl)-3-ethylcarbodiimide hydrochloride (2.3 g) and dichloroacetic acid (0.43 mL) and the resulting solution allowed to stir for 2 hours. The reaction mixture was poured into ethyl acetate, washed (1N hydrochloric acid, $H_2O$), dried, and evaporated. The resulting material was purified by chromatography, with methanol:dichloromethane (3:97) as the eluent. The resulting solid was recrystallized from ethyl acetate to give the title compound (0.41 g); mp 218°-219° C.

Analysis for $C_{22}H_{21}F_3N_3O_5$: Calculated: C, 56.77; H, 4.76; N, 9.03; Found: C, 56.68; H, 4.72; N, 8.77.

The intermediate alcohol was prepared as follows.

a. Ethyl 1-oxo-1,2,3,4-tetrahydropyrido[3,4-b]indol-8-carboxylate. To a solution of 3-ethoxycarbonyl-2-piperidone in $H_2O$ (300 mL) was added lithium hydroxide (8.4 g) and the resulting solution was stirred for 2 hours. The solution was made acidic by addition of 1N hydrochloric acid (75 mL) to pH 4 and cooled in an ice bath. To this solution was added a solution of the aryl diazonium chloride; made by addition of sodium nitrite (15 g) in $H_2O$ (50 mL) to a slurry of concentrated hydrochloric acid (40 mL), ice (100 g), and ethyl 2-aminobenzoate (23 mL). After stirring at 0° C. for 1.5 hours, the solution was allowed to warm to room temperature and was stirred for 3 h. A precipitate formed, was collected, and was recrystallized from ethyl alcohol to give the hydrazone (33.7 g). A 5 g portion of this material was dissolved in ethanol (90 mL) and concentrated sulfuric acid (10 mL) and heated to reflux for 6 hours. The solution was poured into a slurry of ice and sodium bicarbonate (40 g) and was extracted with dichloromethane. The solution was dried and evaporated. The resulting material was chromatographed, with methanol:dichloromethane (10:90) as the eluent, to give the indole (2.0 g); TLC: $R_f$=0.5, ethyl acetate.

b. Ethyl 1-oxo-9-[2-(trimethylsilyl)ethoxymethyl]-1,2,3,4-tetrahydropyrido[3,4,-b]indol-8-carboxylate. To a solution of ethyl 1-oxo-1,2,3,4-tetrahydropyrido-3,4-b]indol-8-carboxylate (1.29 g) in tetrahydrofuran (500 mL) at 0° C. was added sodium hydride (0.2 g, 60% dispersion in mineral oil), and the resulting solution was allowed to stir 0.5 hour. To this solution was added 2-(trimethylsilyl)ethoxymethyl chloride (0.9 mL), and the resulting solution was allowed to stir overnight. The reaction was quenched by addition of a saturated solution of ammonium chloride, extracted with ethyl acetate, and the combined organic layers were dried and evaporated.. The resulting oil was chromatographed, with dichloromethane:ethyl acetate (60:40) as the eluent to give the alkylated amine (1.13 g), which crystallized upon standing; 75.5 MHz $^{13}C$.

NMR (DMSO-$d_6$, with DMSO as a standard at 39.5 ppm): 166.7, 161.3, 133.5, 128.4, 126.9, 124.3, 121.3, 119.8, 119.2, 73.3, 63.9, 60.9, 20.2, 16.8, 14.0, −1.66 ppm.

c. 2-[8-Ethoxycarbony-9-[2-(trimethylsilyl)ethoxymethyl]-1,2,3,4-tetrahydropyrido[3,4-b]indol-2-yl]-N-(2-tert-butyldimethylsilyloxy-3,3,3-trifluoro-1-isopropylpropyl)acetamide. To a solution of ethyl 1-oxo-9-(2-(trimethylsilyl)-ethoxymethyl]-1,2,3,4-tetrahydropyrido[3,4,-b]indol-8-carboxylate (0.97 g) in tetrahydrofuran at 0° C. was added sodium hydride (0.12 g, 60% dispersion in mineral oil) and the resulting solution was allowed to stir for 0.5 hour. To this solution was added N-(2-tert-butyldimethylsilyloxy-3,3,3-trifluoro-1-isopropylpropyl)-2-iodoacetamide (1.2 g), and the resulting solution was stirred overnight. The reaction was quenched by addition of a saturated solution of ammonium chloride. The solution was extracted with ethyl acetate, and the combined organic layers were dried and evaporated. The resulting oil was purified by chromatography, with ethyl acetate:dichloromethane (gradient, 10:90, 20:80) as the eluent, to give the acetamide (1.65 g) as a clear oil; TLC: $R_f$=0.6, ethyl acetate:dichloromethane (10:90).

d. 2-(8-Ethoxycarbony-9-(2-(trimethylsilyl)ethoxymethyl]-1,2-dihydro-pyrido[3,4-b]indol-2-yl)-N-(2-tert-butyldimethylsilyoxy-3,3,3-trifluoro-1-isopropylpropyl)acetamide. To a solution of 2-(8-ethoxycarbony-9-[2-(trimethylsilyl)-ethoxymethyl]-1,2,3,4-tetrahydropyrido[3,4-b]indol-2-yl)-N-(2-tert-butyldimethylsilyloxy-3,3,3-trifluoro-1-isopropylpropyl)acetamide (17.8 g) in dioxane (200 mL) was added 2,3-dichloro-5,6-dicyano-1,4-benzoquinone (7.95 g) and the reaction was allowed to stir for 100 hours. The solvent was removed by evaporation and the resulting residue was dissolved in ether and washed (1N sodium hydroxide, $H_2O$). The solution was dried and the solvent was evaporated to give the 3,4-dehydro compound (16.9 g) as a yellow oil; TLC: $R_f$=0.6, ethyl acetate:dichloromethane (10:90).

e. 2-(8-Ethoxycarbonyl-1,2-dihydropyrido[3,4-b]indol-2-yl)-N-(3,3,3-trifluoro-2-hydroxy-1-isopropylpropyl)acetamide. To a solution of 2-(8-ethoxycarbony-9-(2-(trimethylsilyl)-ethoxymethyl]-1,2-dihydropyrido[3,4-b]-indol-2-yl)-N-(2-tert-butyldimethylsilyoxy-3,3,3-trifluoro-1-isopropylpropyl)acetamide (3.4 g) in acetonitrile (20 mL) was added a solution of 48% HF in $H_2O$ (10 mL) and the resulting solution was allowed to stir overnight. The reaction was quenched by pouring into a solution of sodium bicarbonate. The mixture was extracted with ethyl acetate and dried. The solvent was evaporated and the resulting material was purified by chromatography, with dichloromethane:ethyl acetate (gradient, 2:1, 1:1) as the eluent, to give the alcohol (1.07 g) as a white solid;

NMR: 10.6 (s,1), 8.4 (d,1), 8.0 (d,1), 7.97 (d,1), 7.39 (m,2), 7.1 (d,1), 6.56 (d,1), 4.91 (d,1), 4.65 (d,1), 4.46 (q,2), 4.15 (m,1), 3.84 (t,1), 1.85 (m, 1), 1.40 (t,3), 0.93 (m,6).

The intermediate N-(2-tert-butyldimethylsilyloxy-3,3,3-trifluoro-1-isopropylpropyl)-2-iodoacetamide, used in Example 4.c. was prepared as follows.

f. 2-Chloro-N-(3,3,3-trifluoro-2-hydroxy-1-isopropylpropyl)acetamide. To a solution of 3-amino-1,1,1-trifluoro-4-methyl-2-pentanol hydrochloride (20 g) in distilled tetrahydrofuran (480 mL) under nitrogen was added 4-methylmorpholine (21.8 mL) resulting in a white precipitate. A solution of chloroacetyl chloride (7.7 mL) in distilled tetrahydrofuran (40 mL) was added dropwise over 1 hour, and the mixture was stirred overnight. The mixture was diluted with ethyl acetate and filtered to remove undissolved solids. The filtrate was washed with 10% hydrochloric acid, water, saturated aqueous sodium bicarbonate and brine. The solid that had been filtered was dissolved in water, the aqueous phase was extracted with ethyl acetate (twice), and the extracts were washed as the first extract had been. The organic phases were combined, dried, and evaporated to give 2-chloro-N-(3,3,3-trifluoro-2-hydroxy-1-isopropylpropyl)acetamide as an oil (23.8 g); TLC: $R_f$=0.70, dichloromethane:methanol (95:5); MS: m/z=248(M+1 for $^{35}$Cl).

g. N-(2-tert-Butyldimethylsilyloxy-3,3,3-trifluoro-1-isopropylpropyl)-2-chloroacetamide. 2-Chloro-N-(3,3,3-trifluoro-2-hydroxy-1-isopropylpropyl)acetamide prepared as above (23.79 g) and used directly was dissolved in dichloromethane (96 mL), and 2,6l-lutidine (22.5 mL) was added. tert-Butyldimethylsilyl trifluoromethanesulfonate (33 mL) was added rapidly dropwise. The reaction exothermed vigorously, producing white smoke. Cooling is advised. The mixture was stirred overnight; diluted with ethyl acetate (500 mL); and washed with 10% hydrochloric acid (twice), saturated aqueous sodium bicarbonate, and brine. The ethyl acetate solution was adsorbed onto silica gel (120 mL) by evaporation and chromatographed, eluting with hexane:ethyl acetate (gradient, 100:0, 93:7, 85:15 and 80:20), to afford N-(2-tert-butyldimethylsilyloxy-3,3,3-trifluoro-1-isopropylpropyl)-2-chloroacetamide as a white solid (20.49 g); TLC: $R_f$=0.19, hexane:ethyl acetate (9:1); MS: m/z=362(M+1, $^{35}$Cl).

h. N-(2-tert-Butyldimethylsilyloxy-3,3,3-trifluoro-1-isopropylpropyl)-2-iodoacetamide. N-(2-tert-Butyldimethylsilyloxy-3,3,3-trifluoro-1-isopropyl-propyl)-2-chloroacetamide (15.56 g) was added to a solution of NaI (19.3 g) in acetone (130 mL). The mixture was stirred overnight and the yellow reaction mixture was diluted with water (180 mL). The resulting precipitate was filtered; washed with water and saturated aqueous sodium thiosulfate; and dried under vacuum at 40° C. overnight. After spectral data indicated the presence of starting material, the product was subjected to another iteration of the above reaction conditions. The subsequent work-up was identical except that no sodium thiosulfate wash was performed. Purification by chromatography, eluting with hexane:ethyl acetate (gradient, 80:20 and 50:50), and drying under vacuum afforded N-(2-tert-butyldimethylsilyloxy- 3,3,3-trifluoro-1-isopropylpropyl)-2-iodoacetamide (17.91 g); TLC: $R_f$=0.30, hexane:ethyl acetate (9:1); MS: m/z=454(M+1 for $^{35}$Cl).

EXAMPLE 5.

2-(8-Carboxy-1,2,3,4-tetrahydropyrido[3,4-b]indol-2-yl)-N-(3,3,3-trifluoro-1-isopropyl-2-oxopropyl)acetamide 2-(8-Carboxy-1,2,3,4-tetrahydropyrido[3,4-b]indol-2-yl)- N-(3,3,3-trifluoro-2-hydroxy-1-isopropylpropyl)acetamide was subjected to a procedure similar to that described in Example 4 to provide the title compound, after recrystallization from ethyl acetate; mp 246° C.: MS: m/z=440(M+1).

The intermediate alcohol was prepared as follows.

To a solution of the product from Example 4.c. (1.65 g) in tetrahydrofuran (10 mL) was added tetrabutylammonium fluoride (7 mL, 1M in tetrahydrofuran). The resulting solution was heated at 120° C. for 24 hours. The mixture was diluted with ethyl acetate, washed (water), dried, and evaporated to give a solid, which was triturated with ethyl acetate to give 2-(8-carboxy-1,2,3,4-tetrahydropyrido[3,4-b]indol-2-yl)-N-(3,3,3-trifluoro-2-hydroxy-1-isopropylpropyl)acetamide (0.45 g) as a white solid; MS: m/z=442(M+1).

EXAMPLE 6.

2-(8-Carboxy-1,2-dihydropyrido[3,4-b]indol-2-yl)-N-(3,3,3-trifluoro-1-isopropyl-2-oxopropyl)acetamide 2-(8-Carboxy-1,2,3,4-tetrahydropyrido[3,4-b]indol-2-yl)-N-(3,3,3-trifluoro-1-isopropyl-2-oxopropyl)acetamide (0.14 g) was dissolved in dioxane (50 mL), and 2,3-dichloro-5,6-dicyano-1,4-benzoquinone (0.45 g) was added. The resulting solution was allowed to stir overnight. Ethyl acetate (150 mL) was added and the solution was washed (H$_2$O, brine), dried, and evaporated. The resulting solid was recrystallized from ethyl acetate to give the title compound (0.056 g); mp 260–262° C.

Analysis for $C_{21}H_{18}F_3N_3O_5$: Calculated: C, 54.92; H, 4.15; N, 9.61; Found: C, 54.36; H, 4.24; N, 9.27.

EXAMPLE 7.

2-(8-Carbamoyl-1,2-dihydropyrido[3,4-b]indol-2-yl)-N-(3,3,3-trifluoro-1-isopropyl-2-oxopropyl)acetamide 2-(8-Carbamoyl-1,2-dihydropyrido[3,4-b]indol-2-yl)-N-(3,3,3-trifluoro-2-hydroxy-1-isopropylpropyl)acetamide was subjected to a procedure similar to that described in Example 4. The resultant material was chromatographed, with methanol:dichloromethane as the eluent, to give the title compound; mp 316° C.; MS: m/z=437(M+1).

The intermediate alcohol was prepared as follows.

a. 2-(8-Carboxy-1,2-dihydropyrido[3,4-b]indol-2-yl)-N-(3,3,3-trifluoro-2-hydroxy-1-isopropylpropyl)acetamide. 2-(8-Ethoxycarbonyl-1,2-dihydropyrido[3,4-b]indol-2-yl)-N-(3,3,3-trifluoro-2-hydroxy-1-isopropylpropyl)acetamide was subjected to a hydrolysis procedure similar to that outlined in Example 3 to give the title compound as a white solid;

NMR: 10.4 (s,1), 8.36 (d,1), 8.05 (m,2), 7.35 (m,2), 7.09 (d,1), 4.86 (d,1), 4.63 (d,1), 4.11 (m,1), 3.82 (t,1), 1.77 (m,1), 0.90 (m,6).

b. 2-(8-Carbamoyl-1,2-dihydropyrido[3,4-b]indol-2-yl)-N-(3,3,3-tri-fluoro-2-hydroxy-1-isopropylpropyl)acetamide. To a solution of -2-(8-carboxy-1,2-dihydropyrido[3,4-b]-indol-2-yl)-N-(3,3,3-trifluoro-2-hydroxy-1-isopropylpropyl)acetamide (0.6 g) in dimethylformamide (10 mL) was added a complex of ammonia:hydroxy benzotriazole (0.38 g) and 1-(3-dimethylaminopropyl)-3-ethylcarbodiimide hydrochloride (0.54 g). The resulting solution was allowed to stir for 12 hours. The mixture was diluted with ethyl acetate, washed (saturated ammonium chloride, saturated NaHCO$_3$, H$_2$O), dried, and evaporated to give 2-(8-carbamoyl-1,2-dihydropyrido[3,4-b]indol-2-yl)-N-(3,3,3-trifluoro-2-hydroxy-1-isopropylpropyl)acetamide (0.4 g); MS: m/z=439(M+1).

EXAMPLES 8-13

Using a sequence similar to that described in Example 4 and outlined in Scheme II, the following compounds of formula I wherein $R^0$ is isopropyl, $R^2$ is hydrogen, $R^6$ is hydrogen, and $R^1$, $R^3$, $R^4$ and $R^5$ have the indicated values were prepared.

Example 8. $R^1$=hydrogen, $R^3$=hydrogen, $R^4$=hydrogen, $R^5$=hydrogen; mp 199°–201° C.

Analysis for $C_{19}H_{20}F_3N_3O_3$: Calculated: C, 57.72; H, 5.10; N, 10.63; Found: C, 57.87; H, 5.11; N, 10.61.

Example 9. $R^1$=hydrogen, $R^3$=chloro, $R^4$=hydrogen, $R^5$=hydrogen; mp 242° C.

Analysis for $C_{19}H_{19}ClF_3N_3O_3$: Calculated: C, 53.09; H, 4.46; N, 9.78; Found: C, 52.78; H, 4.54; N, 9.67.

Example 10. $R^1$=hydrogen, $R^3$=methoxy, $R^4$=hydrogen, $R^5$=hydrogen; mp 244–245° C.

Analysis for $C_{20}H_{22}F_3N_3O_4$: Calculated: C, 56.47; H, 5.21; N, 9.88; Found: C, 56.50; H, 5.36; N, 9.93.

Example 11. $R^1$=hydrogen, $R^3$=hydrogen, $R^4$ and $R^5$ together=a double bond; mp 278° C.

Analysis for $C_{19}H_{18}F_3N_3O_3$: Calculated: C, 58.01; H, 4.61; N, 10.68; Found: C, 58.03; H, 4.56; N, 10.55.

Example 12. $R^1$=hydrogen, $R^3$=chloro, $R^4$ and $R^5$ together=a double bond; mp 293–295° C.

Analysis for $C_{19}H_{17}Cl_1F_3N_3O_3.0.5\ H_2O$: Calculated: C, 52.24; H, 4.15; N, 9.62; Found: C, 52.20; H, 3.95; N, 9.60.

Example 13. $R^1$=hydrogen, $R^3$=methoxy, $R^4$ and $R^5$ together=a double bond; mp 248–250° C.

Analysis for $C_{20}H_2OF_3N_3O_4.0.3\ H_2O$: Calculated: C, 55.94; H, 4.85; N, 9.79; Found: C, 55.97; H, 4.73; N, 9.70.

EXAMPLES 14-26

Using a sequence similar to that described in Example 1 and outlined in Scheme I, the following compounds of formula I wherein; $R^4$ and $R^5$ taken together form a double bond, and $R^1$, $R^2$, $R^3$ and $R^6$ have the indicated values were prepared.

Example 14. $R^1$=hydrogen, $R^2$=ethoxycarbonyl, $R^3$=hydrogen, $R^6$=hydrogen; mp 255°–256° C.

Analysis for $C_{22}H_{22}F_3N_3O_5.0.6\ H_2O$: Calculated: C, 55.48; H, 4.91; N, 8.82; Found: C, 55.52; H, 4.84; N, 8.69.

Example 15. $R^1$=hydrogen, $R^2$=carboxy, $R^3$=hydrogen, $R^6$=hydrogen; mp 281°–283° C.

Analysis for $C_{20}H_{18}F_3N_3O_5$: Calculated: C, 54.92; H, 4.14; N, 13.03; Found: C, 54.80; H, 4.01; N, 12.88.

Example 16. $R^1$=hydrogen, $R^2$=hydrogen, $R^3$=hydrogen, $R^6$=isopropyl; mp 256° C.

Analysis for $C_{22}H_{24}F_3N_3O_3$: Calculated: C, 60.68; H, 5.55; N, 9.64; Found: C, 60.51; H, 5.41; N, 9.35.

Example 17. $R^1$=hydrogen, $R^2$=hydrogen, $R^3$=hydrogen, $R^6$=phenyl; mp 317°–319° C.

Analysis for $C_{25}H_{22}F_3N_3O_3.0.3\ H_2O$: Calculated: C, 63.23; H, 4.79; N, 8.84; Found: C, 63.09; H, 4.61; N, 8.52.

Example 18. $R^1$=methylsulfonyl, $R^2$=hydrogen, $R^3$=hydrogen, $R^6$=phenyl; mp 255°–256° C.

Analysis for $C_{26}H_{24}F_3N_3O_6S$: Calculated: C, 55.41; H, 4.29; N, 7.46; Found: C, 55.08; H, 4.41; N, 7.27.

Example 19. $R^1$=methylcarbonyldioxy, $R^2$=hydrogen, $R^3$=hydrogen, $R^6$=phenyl; mp 246°–247° C.

Analysis for $C_{27}H_{24}F_3N_3O_6$: Calculated: C, 59.67; H, 4.45; N, 7.73; Found: C, 59.57; H, 4.57; N, 7.61.

Example 20. $R^1$=methoxy, $R^2$=hydrogen, $R^3$=hydrogen, $R^6$=phenyl; mp 244°–246° C.

Analysis for $C_{26}H_{24}F_3N_3O_4.0.25\ H_2O$: Calculated: C, 61.96; H, 4.90; N, 8.34; Found: C, 61.86; H, 5.04; N, 8.27.

Example 21. $R^1$=carboxy, $R^2$=hydrogen, $R^3$=hydrogen, $R^6$=isopropy.

Analysis for $C_{23}H_{24}O_5N_3F_3.1.0\ H_2O$: Calculated: C, 55.53; H, 5.26; N, 8.44; Found: C, 55.31; H, 5.09; N, 8.29.

Example 22. $R^1$=cyano, $R^2$=hydrogen, $R^3$=hydrogen, $R^6$=isopropyl.

Analysis for $C_{23}H_{23}F_3N_4O_3$: Calculated: C, 59.99; H, 5.03; N, 12.16; Found: C, 59.57; H, 5.12; N, 11.86.

Example 23. $R^1$=methoxycarbonyl, $R^2$=hydrogen, $R^3$=hydrogen, $R^6$=phenyl; mp 228°–231° C.

Analysis for $C_{27}H_{24}F_3N_3O_5$: Calculated: C, 61.47; H, 4.38; N, 7.96; Found: 61.36; H, 4.74; N, 7.75.

Example 24. $R^1$=hydroxy, $R^2$=hydrogen, $R^3$=hydrogen, $R^6$=phenyl; mp 344° C.

Analysis for $C_{25}H_{22}F_3N_3O_4.0.3\ H_2O$: Calculated: C, 61.17; H, 4.68; N, 8.56; Found: C, 60.92; H, 4.84; N, 8.21.

Example 25. $R^1$=dimethoxyphosphoryl, $R^2$=hydrogen, $R^3$=hydrogen, $R^6$=phenyl; mp 149°–150° C.

Analysis for $C_{27}H_{27}N_3F_3O_6P$: Calculated: C, 56.05; H, 4.87; N, 7.26; Found: C, 55.89; H, 4.72; N, 7.11.

Example 26. $R^1$=hydrogen, $R^2$=hydrogen, $R^3$=dimethoxyphosphorpl, $R^6$=phenyl; mp 248°–250° C.

Analysis for $C_{27}H_{27}N_3F_3O_6P$: Calculated: C, 56.05; H, 4.87; N, 7.26; Found: C, 55.71; H, 4.61; N, 7.05.

FORMULAE

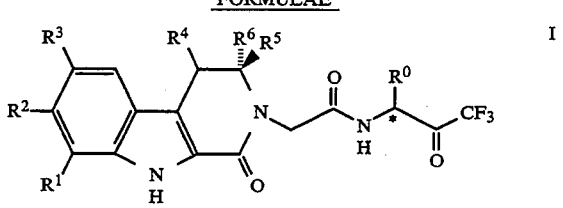

I

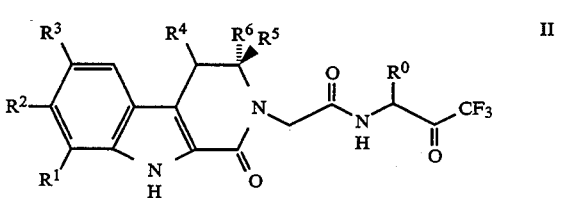

II

Scheme I
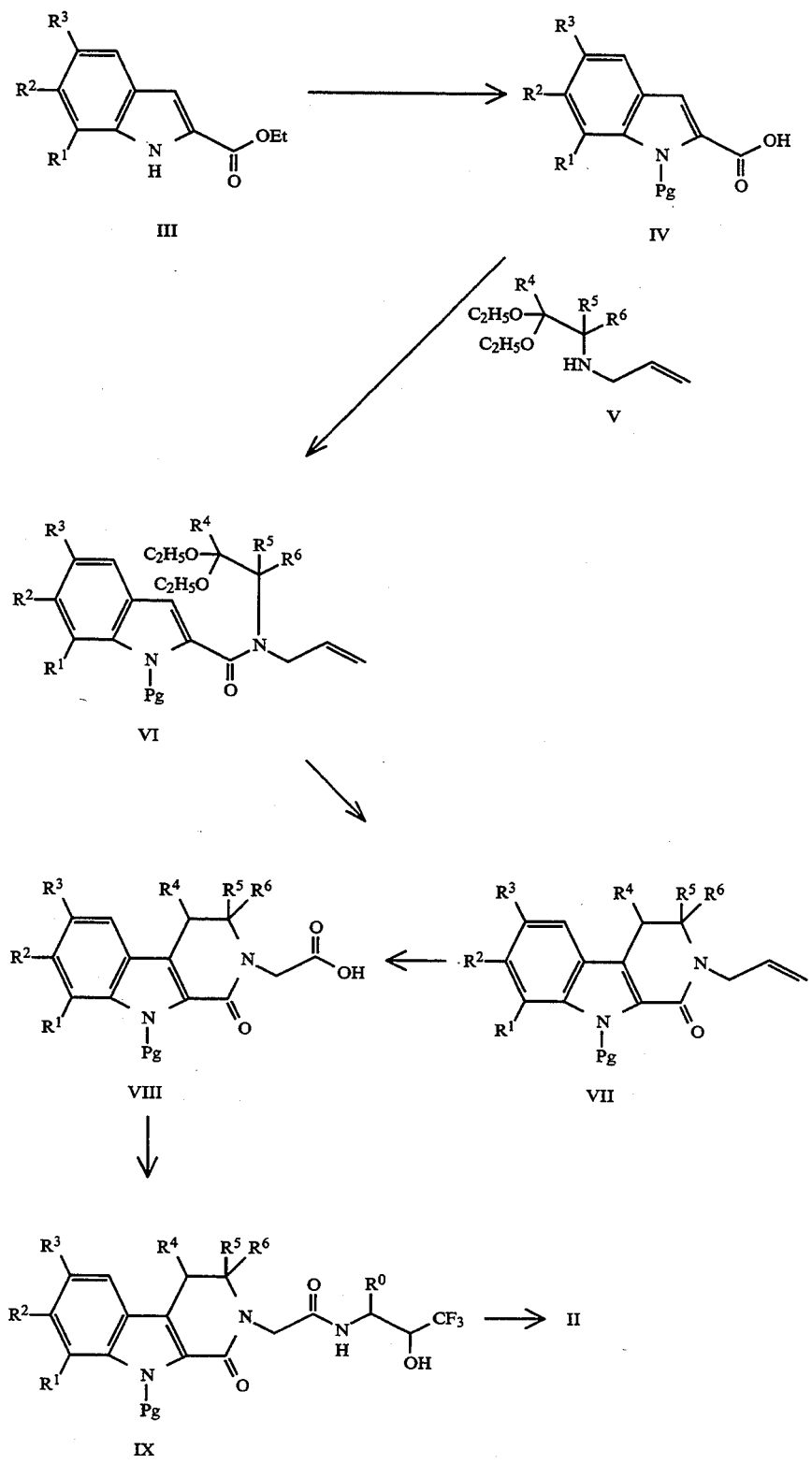

Scheme II

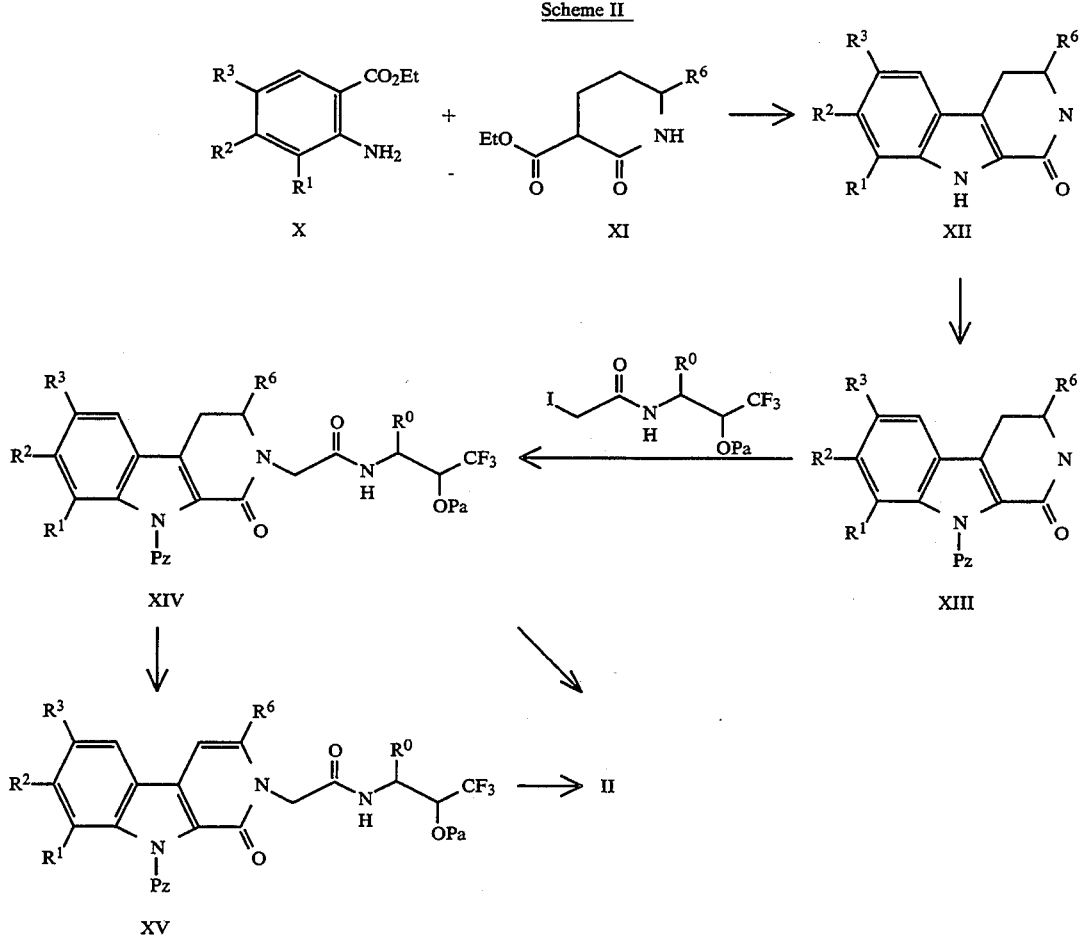

What is claimed is:
1. A compound of formula I wherein:

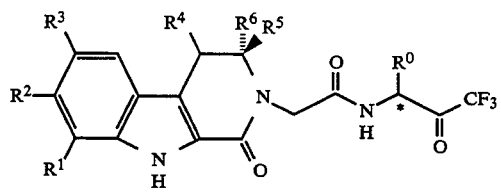

$R^0$ is (1–5C)alkyl;
$R^1$ is selected from a group consisting of cyano, carbamoyl, formyl, hydroxy, (1–4C)alkoxy, methanesulfonyloxy, methanesulfonyl, $(ReO)_2P(O)$, COORf and RgOCOO; and $R^2$ and $R^3$ are hydrogen; or
$R^1$ is hydrogen; $R^2$ is selected from a group consisting of hydrogen, XCOORh and XCONRiRj; and $R^3$ is selected from a group consisting of hydrogen, halogeno, hydroxy, (1–4C)alkoxy, $(RkO)_2P(O)$, COORm and CONRnRp;
$R^4$ is hydrogen; and $R^5$ and $R^6$ are independently selected from a group consisting of hydrogen, (1–6C)alkyl, (3–6C) cycloalkyl or a radical of formula BY— in which B is aryl selected from phenyl, indenyl or napthyl or heteroaryl selected from furyl, imidazolyl, tetrazolyl, pyridyl or an N-oxide thereof, thienyl, pyrimidinyl or an N-oxide thereof, indolyl, quinolinyl or an N-oxide thereof and wherein said B aryl or heteroaryl is unsubstituted or optionally substituted with one or two substituents independently selected from the group consisting of amino, halogeno, nitro, (1–6C) alkyl, (3–6C) cycloalkyl, trifluoromethyl, cyano, hydroxy, (1–4C)alkoxy, —O(CO(1–5C)alkyl, $SO_2Ra$, COORb, CONRcRd; or
$R^4$ and $R^5$ together form a double bond, and $R^6$ is defined as above; and wherein
Rb-Rd, Rf, Rh-Rj and Rm-Rp are independently hydrogen or (1–4C)alkyl;
Re and Rk are independently selected from hydrogen, methyl or ethyl;
Ra and Rg are independently (1–4C) alkyl;
X is either a direct bond or is methylene; and
Y is a direct bond, methylene, ethylene, or trans-vinylene; or
for a compound of formula I which is acidic or basic, a pharmaceutically acceptable salt thereof.

2. A compound as claimed in claim 1 wherein $R^1$ is selected from a group consisting of cyano, carbamoyl, formyl, methanesulfonyloxy, methanesulfonyl, $(ReO)_2P(O)$, COORf and RgOCOO; and $R^2$ and $R^3$ are hydrogen; or
$R^1$ is hydrogen; $R^2$ is selected from a group consisting of hydrogen, XCOORh and XCONRiRj; and $R^3$ is selected from a group consisting of hydrogen, halogeno, hydroxy, (1–4C)alkoxy, $(RkO)_2P(O)$, COORm and CONRnRp.

3. A compound as claimed in claims 1 or 2 wherein $R^0$ is ethyl or isopropyl; (1–4C)alkyl is methyl, ethyl, propyl, isopropyl, butyl, isobutyl, or tert-butyl; (1–6C)alkyl is methyl, ethyl, propyl, isopropyl, butyl, isobutyl, tert-butyl, pentyl, 3-methylbutyl, 1-ethylpropyl, hexyl or 4-methylpentyl; (3–6C)cycloalkyl is cyclopropyl, cyclopentyl or cyclohexyl; aryl is phenyl, indenyl or naphthyl; heteroaryl is furyl, imidazolyl, tetrazolyl, pyridyl or its N-oxide, thienyl, pyrimidinyl or its N-oxide, indolyl or quinolinyl or its N-oxide; —O(CO)(1–5C)alkyl is acetoxy; (1–4C)alkoxy is methoxy, ethoxy, propoxy, isoproxy or t-butoxy; and halogeno is bromo, chloro or fluoro; $R^1$ is hydrogen, carboxy, formyl or methylsulfonyl; $R^2$ hydrogen, carboxymethyl or methoxy; $R^3$ is hydrogen, dimethoxyphosphoryl or chloro; and $R^6$ is hydrogen, phenyl or isopropyl.

4. A compound as claimed in claim 3 wherein $R^0$ is isopropyl; $R^1$ is hydrogen or carboxy; $R^3$ is hydrogen or dimethoxyphosphoryl; and $R^6$ is hydrogen or phenyl.

5. A compound as claimed in claim 1 wherein $R^0$ is isopropyl; $R^1$ is carboxy; $R^4$ and $R^5$ are hydrogen or taken together form a double bond; and $R^6$ is hydrogen or phenyl in which the phenyl may bear one or two halogeno, trifluoromethyl, methyl, hydroxy, methoxy, tert-butoxy, methoxycarbonyl or carboxy substituents.

6. A compound as claimed in claim 5 wherein $R^6$ is phenyl.

7. A compound as claimed in claim 1 wherein $R^0$ is isopropyl; $R^1$ is hydrogen; and $R^6$ is phenyl in which the phenyl may bear one or two halogeno, trifluoromethyl, methyl, hydroxy, methoxy, tert-butoxy, methoxycarbonyl or carboxy substituents.

8. A compound as claimed in claim 7 wherein $R^6$ is phenyl.

9. A salt as claimed in claim 1 selected from
(a) for an acidic compound of formula I, an alkalai metal salt, an alkaline earth metal salt, an aluminium salt, an ammonium salt, or a salt made from a pharmaceutically acceptable organic base; and
(b) for a basic compound of formula I, an acid-addition salt made with an acid which provides a pharmaceutically acceptable anion.

10. A compound of formula II

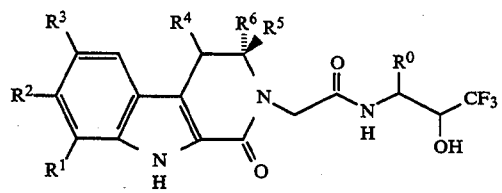

wherein $R^0$–$R^6$ Ra-Rk and Rm-Rp are defined as in claim 1, or a salt thereof.

11. A pharmaceutical composition comprising a leukocyte elastase inhibiting effective amount of a compound as defined in claim 1, or a pharmaceutically acceptable salt thereof, and a pharmaceutically acceptable diluent or carrier.

12. A method of administering a leukocyte elastase inhibiting effective amount of a compound of claim 1, or a pharmaceutically acceptable salt thereof, to a human in need thereof for treatment of pulmonary emphysema, cystic fibrosis, or chronic bronchitis.

* * * * *